(12) United States Patent
Rabelink et al.

(10) Patent No.: US 6,995,158 B2
(45) Date of Patent: Feb. 7, 2006

(54) PHARMACEUTICAL PREPARATION CONTAINING AT LEAST FOLIC ACID OR A FOLATE AND TETRAHYDROBIOPTERIN (BH4) OR DERIVATIVES THEREOF USED FOR THE TREATING OR PREVENTING CARDIOVASCULAR OR NEUROLOGICAL DISORDERS BY MODULATION OF THE ACTIVITY OF NITRIC OXIDE SYNTHASE (NOS)

(75) Inventors: Tom J. Rabelink, Utrecht (NL); Rudolf Moser, Schaffhausen (CH)

(73) Assignee: Eprov A.G., Schaffhausen (CH)

( * ) Notice: Subject to any disclaimer, the term of this patent is extended or adjusted under 35 U.S.C. 154(b) by 0 days.

(21) Appl. No.: 10/377,618

(22) Filed: Mar. 4, 2003

(65) Prior Publication Data

US 2003/0216400 A1 Nov. 20, 2003

Related U.S. Application Data

(62) Division of application No. 09/588,301, filed on Jun. 7, 2000, now Pat. No. 6,544,994.

(51) Int. Cl.
*A61K 31/50* (2006.01)
*A61K 31/195* (2006.01)

(52) U.S. Cl. ................................. 514/249; 514/565
(58) Field of Classification Search ................ 514/249, 514/565
See application file for complete search history.

(56) References Cited

U.S. PATENT DOCUMENTS

| 4,752,573 A | 6/1988 | Ziegler et al. |
|---|---|---|
| 5,502,050 A | 3/1996 | Gross |
| 6,117,872 A | 9/2000 | Maxwell et al. |
| 6,544,994 B2 * | 4/2003 | Rabelink et al. ............ 514/249 |

OTHER PUBLICATIONS

M.C. Verhaar et al., "5-Methyltetrahydrogolate, the Active Form of Folic Acid, Restores Endothelial Function in Familial Hypercholesterolemia," *Circulation*, 97(3): 1998, pp. 237-241.

* cited by examiner

*Primary Examiner*—Raymond J. Henley, III
(74) *Attorney, Agent, or Firm*—Millen White Zelano & Branigan, P.C.

(57) ABSTRACT

The invention relates to the uses of at least folic acid or a folate and tetrahydrobiopterin ($BH_4$) or derivative thereof for treating or preventing cardiovascular of neurological disorders by modulation of the activity of nitric oxide synthase (NOS).

6 Claims, 7 Drawing Sheets

PHARMACEUTICAL PREPARATION CONTAINING AT LEAST FOLIC ACID OR A FOLATE AND TETRAHYDROBIOPTERIN (BH4) OR DERIVATIVES THEREOF USED FOR THE TREATING OR PREVENTING CARDIOVASCULAR OR NEUROLOGICAL DISORDERS BY MODULATION OF THE ACTIVITY OF NITRIC OXIDE SYNTHASE (NOS)

This application is a divisional of application Ser. No. 09/588,301, filed Jun. 7, 2000, now U.S. Pat. No. 6,544,994.

The invention relates to the use of at least folic acid or a folate and tetrahydrobiopterin ($BH_4$) or derivatives thereof for treating or preventing cardiovascular or neurological disorders by modulation of the activity of nitric oxide synthase (NOS). The present invention also relates to the use of at least folic acid or a folate and tetrahydrobiopterin ($BH_4$) or derivatives thereof for the production of a pharmaceutical preparation suitable for influencing the nitric oxide (NO) level, particularly by modulation of the activity of nitric oxide synthase (NOS) by reducing superoxide ($O_2$) production and enhancing nitric oxide (NO) synthesis. This effect occurs in the absence of any negative changes in other risk factors, e.g. lipids, blood pressure and homocysteine. Clinical areas of application include all anomalies of the nitric oxide level, particularly the prevention and treatment of cardiovascular and of neurological disorders. The present invention also relates to pharmaceutical preparations comprising at least one compound selected from the group consisting of 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid, together with tetrahydrobiopterin ($BH_4$) or pharmaceutically compatible salts thereof and with pharmaceutically compatible active and adjuvant substances, such as arginine for influencing the nitric oxide (NO) level.

Within this text the term a folate or a derivative thereof, if not explicitly defined otherwise, always refers to the natural and unnatural stereoisomeric form of each substance, pharmaceutically compatible salts thereof and any mixtures of the isomers and the salts. As drugs, tetrahydrofolates have predominantly been used hitherto as the calcium salt of 5-formyl-5,6,7,8-tetrahydrofolic acid (leucovorin) or of 5-methyl-5,6,7,8-tetrahydrofolic acid (MTHF) for the treatment of megaloblastic folic acid deficiency anemia, as an antidote for increasing the compatibility of folic acid antagonists, particularly of aminopterin and methotrexate in cancer chemotherapy ("antifolate rescue"), for increasing the therapeutic effect of fluorinated pyrimidines and for the treatment of autoimmune diseases such as psoriasis and rheumatoid arthritis, for increasing the compatibility of certain antiparasitic agents, for instance trimethoprim-sulfamethoxazole, and for decreasing the toxicity of dideazatetra-hydrofolates in chemotherapy and for influencing the homocysteine level, particularly for assisting the remethylation of homocysteine.

The term tetrahydrobiopterin ($BH_4$) or a derivative thereof, it not explicitly defined otherwise, always refers to all natural and unnatural stereoisomeric forms of tetrahydrobiopterin, pharmaceutically compatible salts thereof and any mixtures of the isomers and the salts. The term tetrahydrobiopterin also includes any precursors of tetrahydrobiopterin, especially 7,8-dihydrobiopterin. (6R)-tetrahydrobiopterin is a naturally occuring cofactor of the aromatic amino acid hydroxylases and is involved in the synthesis of the three common aromatic amino acids tyrosine, phenylalanine, tryptophan and the neurotransmitters dopamine and serotonin. It is also essential for nitric oxide synthase catalysed oxidation of L-arginine to L-citrullin and nitric oxide. Tetrahydrobiopterin is involved in many other biochemical functions, many of which have been just recently discovered.

The term arginine, if not explicitly defined otherwise, always refers to the natural and unnatural stereoisomeric form of arginine. L-arginine, a natural amino acid, is the precursor of endogenous nitric oxide (NO), which is a ubiquitous and potent vasodilator acting via the intracellular second-messenger cGMP. In healthy humans, L-arginine induces peripheral vasodilation and inhibits platelet aggregation due to an increased NO production. Both an excess and a lack of production of NO have been linked to pathological conditions, including cardiovascular disorders, septic shock, inflammation and infection, and brain damage in stroke and neurological disorders.

The term nitric oxide synthase (NOS), if not explicitly defined otherwise, always refers to all isoforms endothelial nitric oxide synthase (eNOS), neuronal nitric oxide synthase (nNOS) and inducible nitric oxide synthase (iNOS).

Nitric oxide (NO) has been identified as a mediator of atherosclerosis. Therefore it is a therapeutic target in cardiovascular prevention trials. It also plays an important role in neurological disorders. Biological effects of nitric oxide (NO) are not limited to vascular relaxation, but are also important in the respiratory, urogenital and gastrointestinal system, central and peripheral nervous system, neuroendocrine and endocrine systems, and nonspecific immunity.

Nitric oxide (NO) and superoxide ($O_2$) are cytotoxins on their own, yet it has been demonstrated that the two relatively unreactive radicals can rapidly combine ($k=3.7 \times 10^7$ $M^{-1}$ $s^{-1}$) under physiological conditions to the strong oxidizing agent peroxynitrite ($ONOO^-$). This reaction is about 3 times faster than the detoxifying catabolism of superoxide by superoxide dismutase (SOD). It is believed that the formation of peroxynitrite is an important factor in the oxidative damage associated with ischemia/reperfusion. A variety of pathologies are associated with the formation of peroxynitrite. Peroxynitrite is invariably formed in larger amounts when more NO is produced, and/or when an elevated level of superoxide prevails. In this regard, pathologies such as diabetes, atherosclerosis, and ischemia-reperfusion injury, are associated with oxidative stress characterized by an elevated level of superoxide that can lead to increased peroxynitrite formation. Also when glutathione detoxification mechanism against peroxynitrite is impaired critical concentrations of peroxinitrite may occur. Recent evidence also suggests multiple sclerosis and Alzheimer's disease are associated with peroxynitrite formation. In addition, peroxynitrite has also been implicated during sepsis and adult respiratory distress syndrome. Ischemia and reperfusion are accompanied by an increase in superoxide due to the activation of xanthine oxidase and NAPDH oxidase, respectively. Thus, peroxynitrite is likely to be implicated in a number of pathologies in which an imbalance of NO and superoxide occurs.

Several factors can contribute to reduced bioavailability of NO, ranging from impaired production to increased degradation, depending on the risk factors involved. NO is synthesized by dimers of the 130 kD enzyme endothelial NO synthase in a reaction where arginine is oxidized to NO and citrulline. It has been shown that eNOS produces superoxide radicals as well as NO. Under physiological conditions, NOS predominantly produces NO, controlled by the regulatory co-enzyme calmodulin, the substrate arginine and the cofactor tetrahydrobiopterin ($BH_4$). Under pathophysiological conditions, such as dyslipidemia, production shifts from NO to superoxide. Clinical studies have shown impaired NO bio-availability in patients with (risk factors for) atherosclerosis. Evidence has accumulated showing that increased production of superoxide and increased degradation of NO by superoxide, rather than impaired formation of NO is the predominant cause of impaired NO bioavailability in early atherosclerosis. These observations indicate that atherogenesis is linked to a pathological imbalance between NO and superoxide, rather than reduced NO production per se.

The level of superoxide can be lowered by substances showing a relevant scavenging capacity for superoxide radicals. Measurements revealed that arginine does not react with superoxide. However, both arginine and tetrahydrobiopterin ($BH_4$) are required to minimize or abolish superoxide formation by NOS. Tetrahydrobiopterin ($BH_4$) shows a reaction rate with superoxide which is roughly 2 fold smaller than that of the potent antioxidant ascorbic acid and for folic acid, folates or derivatives thereof (as an example 5-methyl-(6S)- and (6R)-tetrahydrofolic acid have been measured), the reaction rates are about 20 times slower than that of ascorbic acid. Beside of its tenfold lower scavenging capacity folic acid, folates or derivatives thereof are different from tetrahydrobiopterin ($BH_4$) or derivatives thereof in that achievable plasma concentrations are far lower. Upon standard oral suppletion of folic acid (5 mg p.o.) systemic plasma concentrations of 5-methyltetrahydrofolic acid up to ca. 150 nM are achieved whereas upon intra-arterial infusion values of 250 nM were reached. Both these interventions have been shown to result in an improvement in NO-availability in hypercholesterolemic patients. Still these levels of folic acid, folates or derivatives thereof remain orders of magnitude below those of ascorbic acid (concentrations up to 50 $\mu$M).

Despite of the situation that it has been known that "a scavenging effect of $BH_4$ had been remarked" [Vasquez-Vivar, J. et al., Proc. Natl. Acad, Sci. U.S.A., 1998, 95, 9220–9225], "exogenous $BH_4$ is capable of restoring impaired NO activity in prehypertensive rats" [Cosentino, F. et al., J. Clin. Invest., 1998, 101, 1530–1537], "exogenous $BH_4$ is capable of restoring impaired NO activity in hypercholesterolemia patients" [Stroes, E. et al., J. Clin. Invest., 1997, 99, 41–46], "exogenous $BH_4$ is capable of restoring impaired NO activity in diabetic patients" [Pieper, G. M., J. Cardiovasc. Pharmacol., 1997, 29, 8–15], "folate therapy improves NO activity during hypercholesterolemia in vivo" [Woo, K. S. et al., Circulation, 1998, 97, 1–165–166] and [Verhaar, M. C. et al., Circulation, 1998; 97 (3), 237–241], "folic acid and its active form 5-MTHF restore impaired NO bioavailability in dyslipidemic conditions" [Wilmink, H. et al., Arteriosclerosis Thromb Vasc Biol, 2000; 20 (1), 185–8] and [Verhaar, M. C. et al., Circulation, 1998; 97 (3), 237–241], "clinical studies have revealed that the impairment of endogenous vasodilator function observed with hypercholesterolemia is reversible by administration of L-arginine" [Creager, M. A. et al., Clin Invest. 1992, 90, 1248–1253] and "Folic acid supplementation improves arterial endothelial function in adults with realtive hyperhomocysteinemia" [Woo, K. S. et al., J. Am. College of Cardiology, 1999, 34 (7), 2002–2006] the use of at least folic acid or a folate and tetrahydrobiopterin ($BH_4$) or derivatives thereof together with pharmaceutically compatible active and adjuvant substances, such as arginine for the production of a pharmaceutical preparation suitable for influencing the nitric oxide (NO) level has neither been proposed nor described hitherto.

This is probably due to the situation that it has been postulated that "MTHF had no direct effect on in vitro NO production by eNOS" [Verhaar, M. C. et al., Circulation, 1998; 97 (3), 237–241].

It has been found that the use of pharmaceutical preparations containing at least folic acid or a folate and tetrahydrobiopterin ($BH_4$) or derivatives thereof influences the nitric oxide (NO) level, and in particular affects the enzymatic activity of nitric oxide synthase (NOS) by reducing superoxide production and enhancing nitric oxide (NO) synthesis. This effect occurs in absence of negative changes in other risk factors, e.g. lipids, blood pressure and homocysteine.

Especially surprising is this effect as in pterin-free eNOS folic acid, a folate or a derivative thereof does not affect the enzymatic activity of nitric oxide synthase (NOS), neither with regard to NO, nor to superoxide production, whereas in partially pterin-repleted eNOS folio acid, a folate or a derivative thereof have the claimed strong effect on the activity of the enzyme; i.e. they enhance NO production concomitant with a decreased production of superoxide. The beneficial vascular effect of folio acid or a folate together with at least tetrahydrobiopterin ($BH_4$) or derivatives thereof cannot be attributed solely to direct scavenging of superoxide.

Folic acid, a folate or a derivative thereof refers to folic acid (pteroylmonoglutamate), one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or pharmaceutically compatible salt thereof or a combination of two or more thereof. Especially means folic acid, a folate or a derivative thereof folic acid, dihydrofolate, tetrahydrofolate, 5-methyltetrahydrofolate, 5,10-methylenetetrahydrofolate, 5,10-methenyltetrahydrofolate, 5,10-formiminotetrahydrofolate, 5-formyltetrahydrofolate (leucovorin), 10-formyltetrahydrofolate 10-methyltetrahydrofolate, pharmaceutically compatible salts thereof, or a combination of two or more thereof.

Reduced folates can be converted into one another according to the well known folate metabolism. 5-methyltetrahydrofolic acid and the pharmaceutically compatible salts thereof are preferably used, however, since 5-methyltetrahydrofolic acid is directly involved together with tetrahydrobiopterin in such functions as the biosynthesis of dopamine, norepinephrine and serotinine by the hydroxylation of phenylalanine and the regeneration of $BH_4$ by the reduction of the quinonoid 7,8-dihydrobiopterin to tetrahydrobiopterin. This applies in particular when there is an existing methylenetetrahydrofolate reductase deficiency, wherein this deficiency implies disorders such as restricted functionality or lack of activity, for example. The existence of thermolabile methylenetetrahydrofolate reductase should be mentioned here as the most frequent example of a methylenetetrahydrofolate reductase deficiency. Under these circumstances, especially 5-methyltetrahydrofolic acid is only available in a limited amount.

Within all folates or a derivatives thereof both the natural and the unnatural diastereoisomers, pharmaceutically compatible salts thereof and any mixtures of the isomers and the salts, but especially the natural diastereoisomeric forms such as 5-methyl-(6S)-tetrahydrofolic acid are applicable.

Tetrahydrobiopterin ($BH_4$) refers to all the natural and the unnatural forms of tetrahydrobiopterin, pharmaceutically compatible salts thereof and any mixtures of the isomers and the salts, but especially the natural diastereoisomeric form (6R)-L-erythro-tetrahydrobiopterin is applicable.

Arginine refers to the both the natural and unnatural isomeric form of arginine, pharmaceutically compatible salts thereof and any mixtures of the isomers and the salts, but especially the natural isomeric form L-arginine is applicable.

Figure 7:
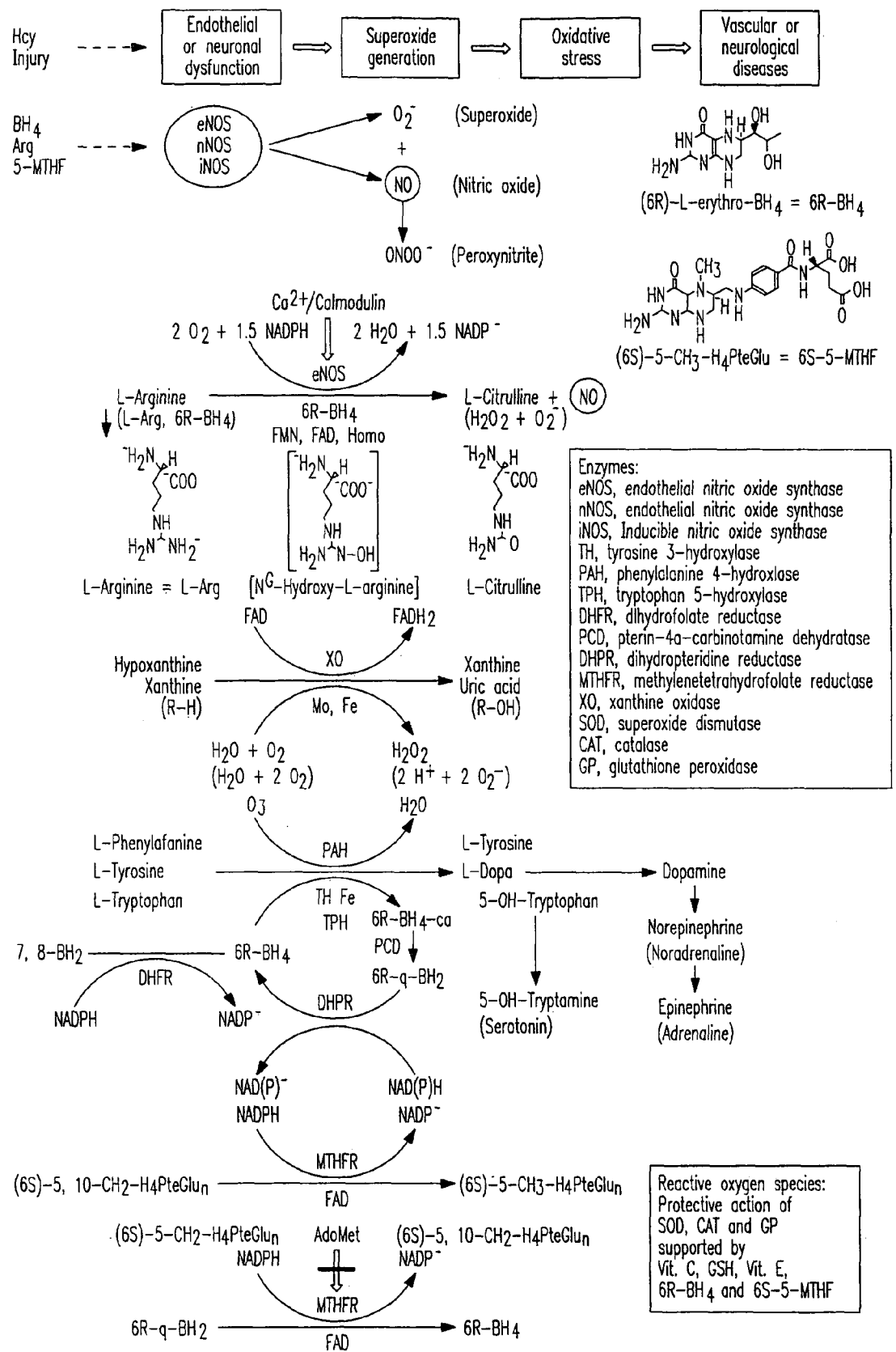
FIG. 7 shows an overview of biochemical functions of folates and tetrahydrobiopterin regarding nitric oxide and oxidative stress.

For an overview of the biochemical functions of folates and tetrahydrobiopterin regarding nitric oxide and oxidative stress see FIG. 7.

Pharmaceutically compatible salts should be both pharmacologically and pharmaceutically compatible. Pharmacologically and pharmaceutically compatible salts such as these may be alkali or alkaline earth metal salts, preferably sodium, potassium, magnesium or calcium salts.

The expression "pharmaceutical preparations" refers to enteral (e.g. oral, sublingual or rectal), parenteral or topical (e.g. transdermal) forms. Organic or inorganic substances which do not react with the active ingredient can be used as supports, e.g. water, oil, benzyl alcohol, polyethylene glycol, glycerol triacetate or other fatty acid glycerides, gelatine, lecithin, cyclodextrin, carbohydrates such as lactobiose or starch, magnesium stearate, talc or cellulose. Tablets, dragees, capsules powders, syrup concentrates or drops are preferred for oral application, suppositories are preferred for rectal application, and water- or oil-based solutions or lyophilisates are preferably used for-parenteral application. Suspensions, emulsions or implants can also be used, and patches or creams can be used for topical application.

Pharmaceutical preparations for parenteral application comprise sterile aqueous and non-aqueous injection solutions of the pharmaceutically-active compounds, which are preferably isotonic with the blood of the recipient.

These preparations may comprise stabilizers, additives for the controlled release of the pharmaceutically-active compounds, antioxidants, such as ascorbic acid, reduced glutathione or N-acetyl-cysteine, buffers, bacteriostatic agents and adjuvant substances for obtaining an isotonic solution. Aqueous and non-aqueous sterile suspensions may contain suspension additives and thickeners. The pharmaceutical preparation may exist as a single dose- or as a multiple-dose container, as sealed ampoules for example, and may be stored as a freeze-dried (lyophilized) product and prepared for use if need be with a sterile liquid, for example water or salt solution. Sterile powders, granules or tablets can be used in the same manner. All the pharmaceutical preparations may additionally contain active compounds which act separately or synergistically. Arginine should be mentioned here, which has a synergistic effect in this application. In this respect, arginine can be used in a dose between 1 mg and 1 g, preferably between 1 mg and 100 mg per day, for a normal dosage application, and can be used in a dose between 10 mg and 1 g per day for a high dosage application.

The pharmaceutical preparation contains between 0.001 mg and 1000 mg of folic acid or a folate and tetrahydrobiopterin ($BH_4$) or derivatives thereof together with 1 mg to 10 g of arginine per dose. In prophylaxis, preparations are used which preferably contain between 5 µg and 1000 mg of the active ingredient per dose. In therapy, preparations are used which preferably contain between 0.1 mg and 200 mg of folic acid or a folate and tetrahydrobiopterin ($BH_4$) or derivatives thereof together with 1 mg to 1 g of arginine per dose.

The dosage depends on the form of therapy, on the form of application of the pharmaceutical preparation, and on the age, weight, nutrition and condition of the patient. Treatment may be commenced with a low dosage below the optimum amount and this may be increased until the optimum effect is achieved. The dosages used in prophylaxis may preferably vary for folic acid or a folate and tetrahydrobiopterin ($BH_4$) between 5 µg and 1000 µg per day, particularly between 50 µg and 500 µg per day. Optimum dosages in therapy vary for folic acid or a folate and tetrahydrobiopterin ($BH_4$) between 0.1 mg and 100 mg per day, particularly between 0.5 mg and 5 mg per day. Application may be effected as a single administration or as a repeated dosage.

EXAMPLES TO ILLUSTRATE THE INVENTION

Chemicals $BH_4$-free bovine eNOS was obtained through expression of eNOS in *E coli*. 5-methyl-(6S)-tetrahydrofolic acid, and its stereoisomer, 5-methyl-(6R)-tetrahydrofolic acid were used in purities >99.8%. The spin trap, 5-diethoxy-phosphoryl-5-methyl-1-pyrroline-N-oxide (DEPMPO) and all other used chemicals are commercially available.

Electron Paramagnetic Resonance Measurements (EPR)

The EPR spectra were recorded at 37° C. on a modified Bruker ESP 300. Spin trap experiments were performed with both HX/XO and eNOS. For HX/XO the solution contained 0.5 mM hypoxanthine, 12.5 mU/ml xanthine oxidase and 50 mM DEPMPO in phosphate buffer (pH 7.4). The eNOS assay contained 250 nM eNOS dimers (0.065 mg protein/ml), 0.5 mM NADPH, 10 µM L-arginine, 1 mM $CaCl_2$, 300 U/ml calmodulin and 50 mM DEPMPO in phosphate buffer (pH 7.4).

Determination of NO-Production by eNOS

NOS activity was determined by quantifying the conversion of L-[2,3,4.5-$^3$H]arginine into L-[2,3,4,5-$^3$H]-citrulline. Briefly, 2 µg eNOS ($BH_4$-free or -repleted) was incubated during 5 min at 37° C. in 100 µl HEPES buffer (pH 7.4) containing DTPA (0.1 mmol/l), $CaCl_2$ (0.2 mmol/l), calmodulin (20 µg/ml), NADPH (0.5 mmol/l), FMN (1 µmol/l), FAD (1 µmol/l), glutathione (100 mmol/l), BSA (200 µg/ml), L-arginine (100 µmol/l), and L-[2,3,4,5-$^3$H]-arginine (3.7 KBq). All measurements were performed in triplicate. After correction for nonspecific activity, eNOS activity was calculated from the percent conversion of [$^3$H]-arginine into [$^3$H]-citrulline and expressed as nmoles per mg protein per min.

Cell Cultures

Microvascular endothelial bEND3 cells were cultured to confluence in 6-well culture plates for determination of nitrite or in 15-cm dishes for electron spin resonance experiments. After the cells reached confluence the medium was changed to M-199 (Sigma chem), supplemented with 0.1% BSA, 5 mM L-glutamine, antibiotics and 5-methyltetrahydrofolic acid (0, 1, 10 µM) or sepiapterin (100 µM), respectively, for 24 hours.

Determination of NO Production by Endothelial Cells

The NO production by endothelial cells was assessed by quantification of the nitrite content in the supernatant with a commercially available fluorimetric kit (Cayman Chemicals). Acetylcholine-induced NO production is presented as the difference between stimulated minus the unstimulated nitrite content.

Statistical Analysis

Figure 3:
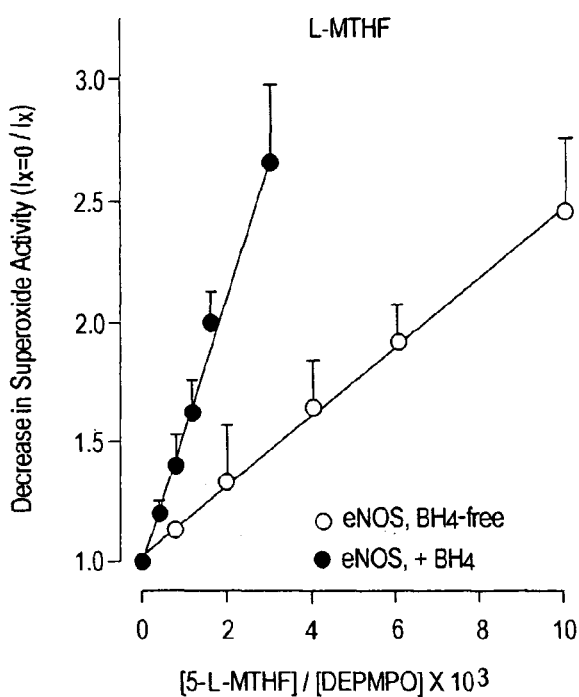
FIG. 3 shows the competitive superoxide trapping by 5-methyl-(6S)- and -(6R)-tetrahydrofolic acid in eNOS. The slope of the curve is much steeper for pterin-repleted (solid circles) than for pterin-free (open circles) eNOS, both for 5-methyl-(6S)- as well as -(6R)-tetrahydrofolic acid ($p<0.05$ pterin-repleted vs. pterin-free eNOS). This shows that 5-methyltetrahydrofolic acid interferes with enzymatic superoxide production by pterin-repleted eNOS.
Figure 3:
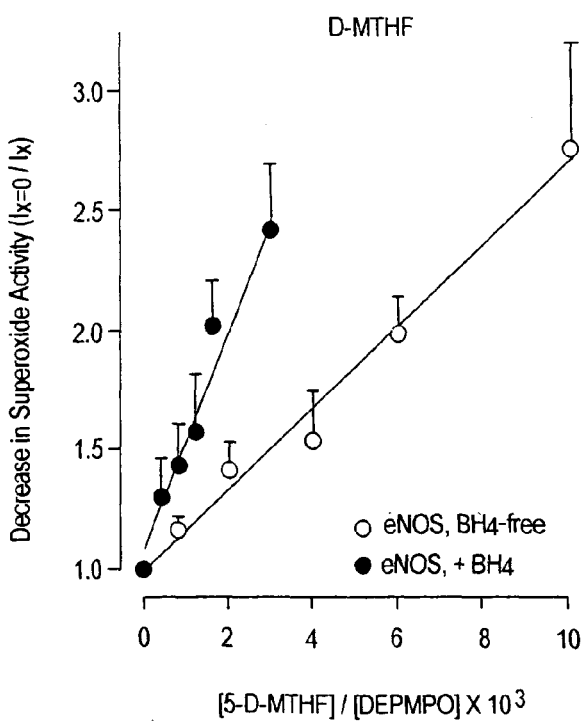

Changes in NO-production were tested with an unpaired t-test. Changes in radical adduct formation by tetrahydrobiopterin (FIG. 3) or 5-methyl-(6S)-tetrahydrofolic acid (FIG. 4) were tested with analysis of variance. If variance ratios reached statistical significance, differences between the means were analyzed with the Student-Newman-Keuls test for $p<0.05$.

5-Methyltetrahydrofolic Acid Direct Superoxide Scavenging

XO Activity

Assessment of urate levels (assessed with a uricase-hydrogen peroxide assay) is a standard method to determine enzymatic activity of XO. However, reductive substance, like vitamin C or NUHF, are known to interfere with the urate determination. Basal urate levels after 60 minutes of incubation (1, 2, 5 mU/ml XO, 0.5 mM hypoxanthine in phosphate buffer, pH 7.4, 37° C.) were 128±20 µM. Addition of 50 µM 5-methyl-(6S)-tetrahydrofolic acid at the beginning of the incubation period resulted in a significantly lower urate level of 48.7±1.7 µM. Addition of 50 µM 5-methyl-(6S)-tetrahydrofolic acid at the end of the incubation period (just prior to urate assessment) resulted in a similar urate level (49.9±1.9 µM). These date show that 5-methyl-(6S)-tetrahydrofolic acid interferes with the quantification of urate, rather than the urate production itself and that 5-methyltetrahydrofolic acid does not affect the rate of urate production by XO.

Determination of Superoxide Trapping Rates by Competitive Superoxide Trapping

Figure 1:
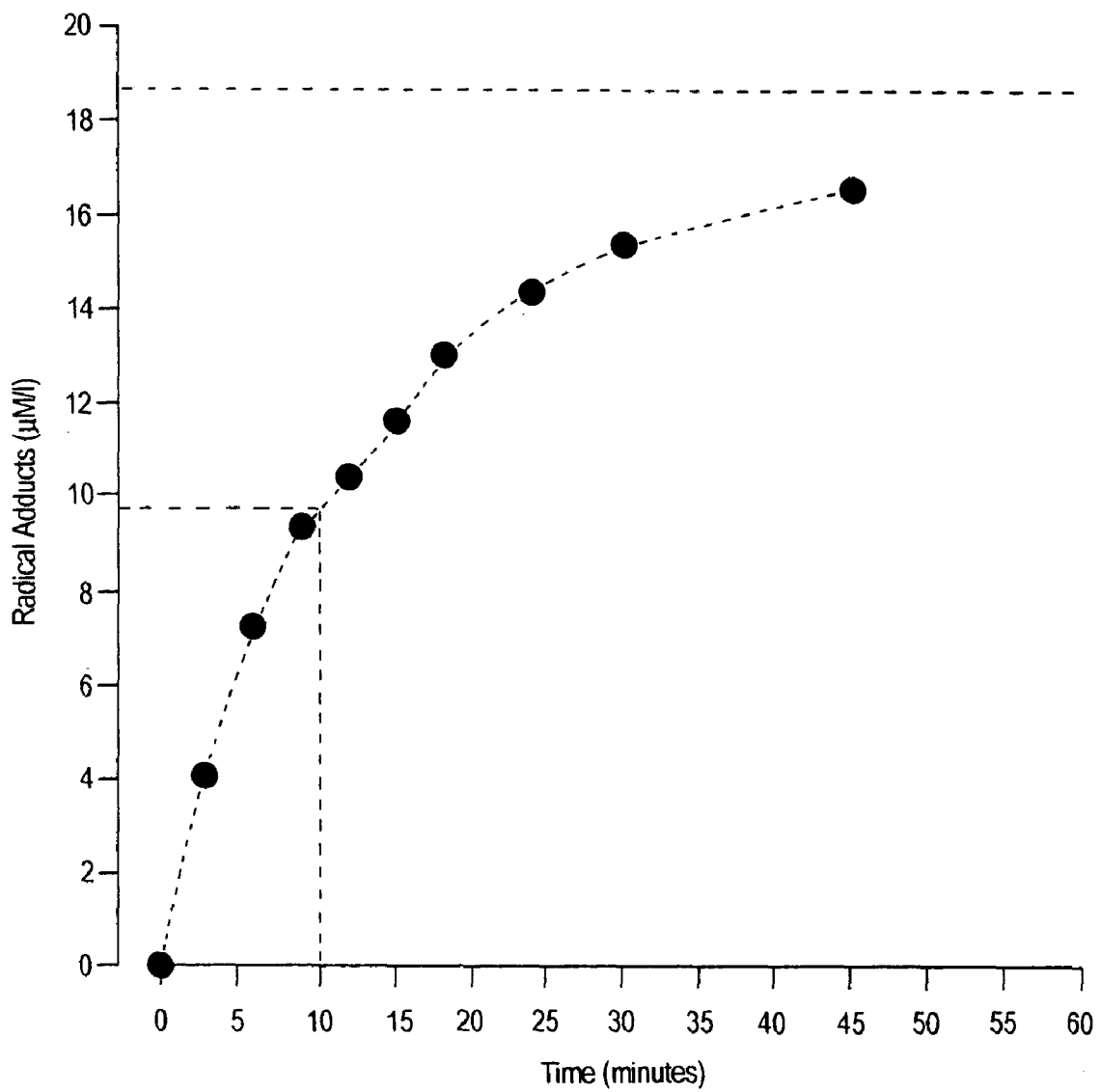
FIG. 1 shows a time-curve of EPR intensity for HX/XO.

The trapping rates for superoxide were determined at 37° C. by comparing the trapping efficiency of L, arginine, tetrahydrobiopterin and 5-methyl-(6S)- and -(6R)-tetrahydrofolic acid with the known trapping efficiency of the spin trap DEPMPO (competitive superoxide trapping [CST]). Using HX/XO as superoxide generating system, the presence of other compound (like L-arginine, tetrahydrobiopterin, 5-methyltetrahydrofolic acid or ascorbic acid) will result in less generation of DEPMPO spin adducts. Reaction channels other than with DEPMPO, L-arginine, tetrahydrobiopterin, 5-methyltetrahydrofolic acid or ascorbic acid can be neglected as the adduct yield does not increase further if DEPMPO concentrations higher than 50 mM are used. The time curves of the EPR intensity in the HX/XO system were described by single exponentials with a time constant, t=10±0.5 min (FIG. 1). Plots of the steady state limits as a function of 5-methyl-(6S)- and -(6R)-tetrahydrofolic acid concentration in the HX/XO system are given in FIG. 2 (solid circles). Both isomers show the same linear concentration dependence.

The reaction rates with superoxide are given by k for the tested substance and $k_d$ for the reference compound DEPMPO respectively. A reference value of $k_d=80$ $(Ms)^{-1}$ has been shown to be reliable. Based thereon the following values have been determined at pH 7.4 and 37° C.

| | | | |
|---|---|---|---|
| $k_{ascorbic\ acid}/k_d$ – | 4400 | $k_{ascorbic\ acid}$ – | $3.5 \times 10^5$ $(Ms)^{-1}$ [literature value] |
| | | $k_{ascorbic\ acid}$ – | $2.7 \times 10^5$ $(Ms)^{-1}$] |
| $k_{BH4}/k_d$ – | 1200 | $k_{BH4}$ – | $1.5 \times 10^6$ $(Ms)^{-1}$ |
| $k_{L-MTHF}/k_d$ – | 150 | $k_{L-MTHF}$ – | $1.2 \times 10^4$ $(Ms)^{-1}$ |
| $k_{D-MTHF}/k_d$ – | 150 | $k_{D-MTHF}$ – | $1.2 \times 10^4$ $(Ms)^{-1}$ |
| $k_{arginine}/k_d$ – | $<10^{-2}$ | $k_{arginine}$ – | neglibile |

The presence of L-arginine did not affect the formation of DEPMPO adducts, even at high concentrations (up to 100 mM). Therefore, L-arginine has no significant scavenging capacity for superoxide.

$BH_4$ is an about 2 times less potent scavenger than ascorbic acid, whereas both isomers of 5-methyltetrahydrofolic acid are in this regard about 20 times less potent than ascorbic acid. In addition the usual plasma concentration for tetrahydrobiopterin and folates are in the low nanomolar range. Upon oral supplementation, the level of folic acid may be raised to micromolar range, which is still below the vitamin C levels of 30–50 micromolar observed in vivo. Therefore due to the low scavenging potency and low plasma concentration of $BH_4$ and folates their direct superoxide scavenging capacity is not relevant in vivo, where antioxidant mechanisms like vitamin C or superoxide dismutase (SOD) have far higher capacity for removal of superoxide. Instead, folates exerts their beneficial effects together with tetrahydrobiopterin through modulation of the enzymatic activity of NOS.

5-Methyltetrahydrofolic Acid-Pterin-Free eNOS

Superoxide Production by Pterin-Free eNOS

Figure 2:
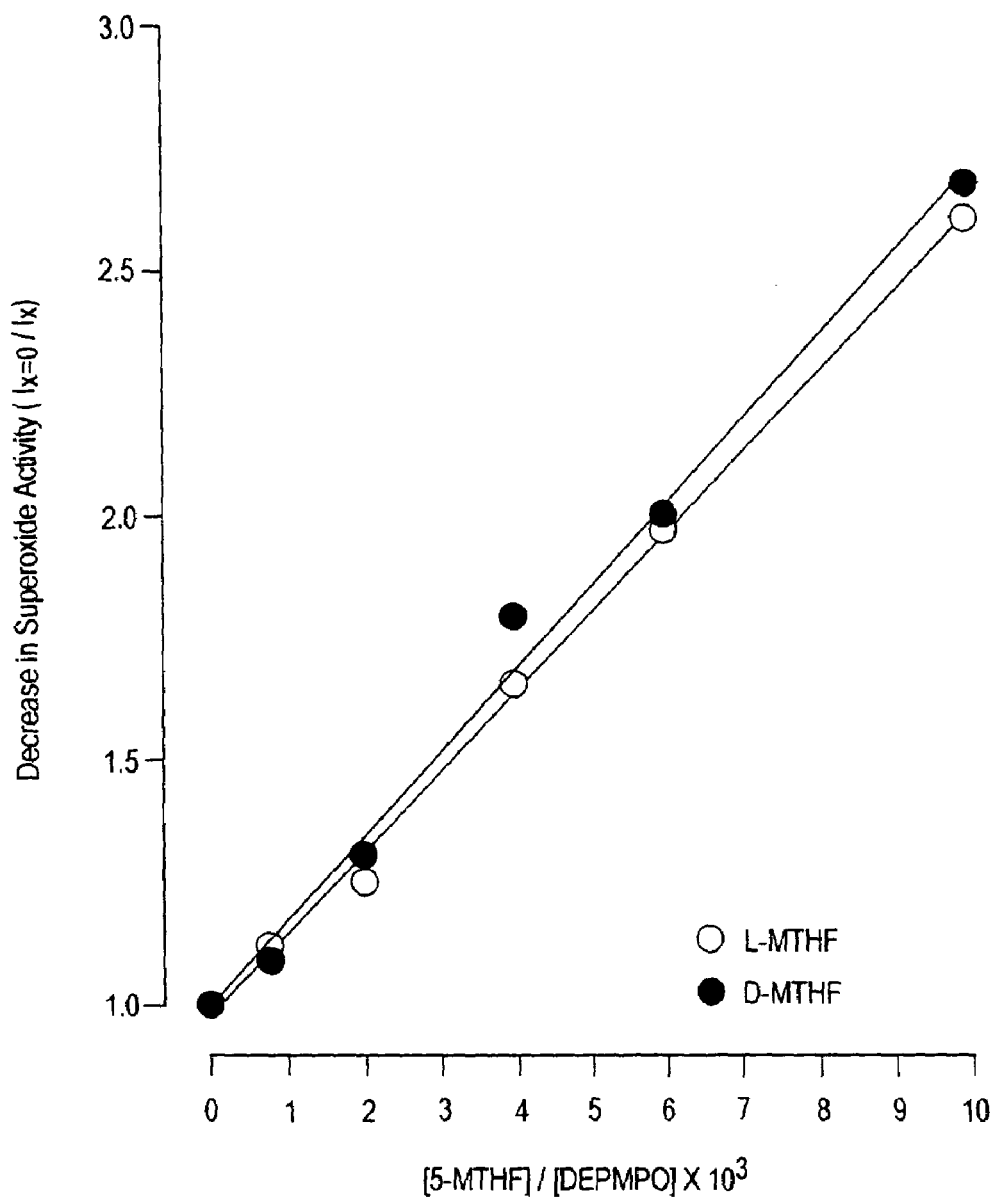
FIG. 2 shows the competitive superoxide trapping by 5-methyl-(6S)- and -(6R)-tetrahydrofolic acid in HX/XO from the slope of the curves it follows that the superoxide trapping rated for 5-methyl-(6S)-tetrahydrofolic acid (open circles) and 5-methyl-(6R)-tetrahydrofolic acid (solid circles) are similar and about 175 times the superoxide trapping rate of DEPMPO.

To elucidate whether that 5-methyl-(6S)-tetrahydrofolic acid improves NO bioavailability in vivo in hypercholesterolemic patients by a direct effect of 5-methyl-(6S)-tetrahydrofolic acid on eNOS, competitive superoxide trapping (CST) experiments using eNOS as a superoxide generating system have been carried aout. The effect of 5-methyl-(6S)- and -(6R)-tetrahydrofolic acid on the pterin-free eNOS (FIG. 3, solid circles) coincides with the data from the HX/XO experiments (c.f. FIG. 2). It demonstrates that for pterin-free eNOS impaired formation of spin adducts can be fully accounted for by the capacity of 5-methyl-(6S)- and -(6R)-tetrahydrofolic acid to scavenge superoxide in a bimolecular scavenging reaction. In particular, the presence of 5-methyl-(6S)- or -(6R)-tetrahydrofolic acid does not affect the rate of superoxide production by pterin-free eNOS.

In pterin-free eNOS, folic acid, a folate or a derivative thereof significantly reduce the formation of DEPMPO superoxide adducts. The degree of reduction in superoxide activity by folic acid, a folate or a derivative thereof is equivalent to that observed in the HX/XO system. It shows that for pterin-free eNOS folic acid a folate or a derivative thereof exerts its effects through pure scavenging only, without interfering with enzymatic activity. Combining the results for NO and superoxide, pterin-free eNOS is seen to be completely oblivious to the presence of folic acid, a folate or a derivative thereof.

5-Methyltetrahydrofolic acid-Pterin-Repleted eNOS

Superoxide Production by eNOS.—Pterin-Repleted Case

Figure 4:
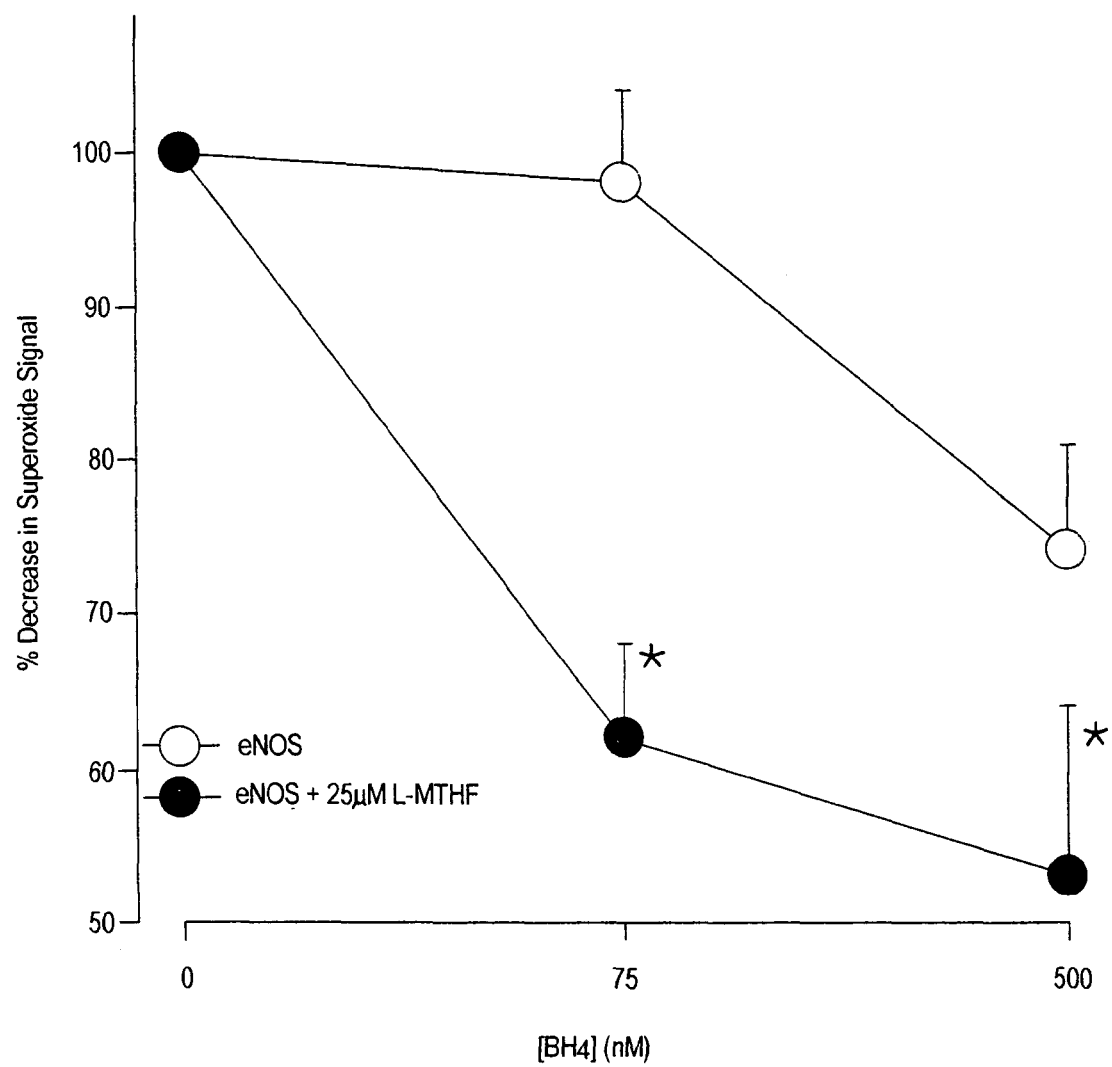
FIG. 4 shows the effect of tetrahydrobiopterin ($BH_4$) on superoxide by eNOS I presence and absence of 5-methyl-(6S)-tetrahydrofolic acid. $BH_4$ induces a dose-dependent decreased in radical-adduct formation (open circles). Preincubator with 5-methyl-(6S)-tetrahydrofolic acid (25 $\mu M$) significantly enhances the $BH_4$-associated decreased in radical adduct formation by eNOS (closed circles).

As far as pterin-repleted eNOS is concerned (FIG. 3, open circles), addition of 5-methyl-(6S)- or -(6R)-tetrahydrofolic acid results in a very strong reduction in the rate of DEPMPO adduct formation (as manifests itself from a much steeper slope). This reduction by far exceeds the reduction observed in pterin-free eNOS. This observation cannot be fully explained by the capacity of 5-methyl-(6S)- and -(6R)-tetrahydrofolic acid to scavenge superoxide. Therefore the presence of 5-methyltetrahydrofolic acid reduces the superoxide production by eNOS in a concentration dependent way with both stereoisomers of 5-methyltetrahydrofolic acid having the same potency. To evaluate whether 5-methyltetrahydrofolic acid only affects eNOS after preincubation with $BH_4$, increasing amounts of $BH_4$ have been added to pterin-free eNOS in presence and absence of 5-methyl-(6S)-tetrahydrofolic acid 25 μM (FIG. 4) As expected, in the absence of 5-methyltetrahydrofolic acid, addition of $BH_4$ caused a dose-dependent decrease in superoxide production. In pterin-free eNOS, addition of 25 μM 5-methyl-(6S)-tetrahydrofolic acid does not cause significant changes in radical adduct formation (FIG. 4). In contrast, addition of 5-methyltetrahydrofolic acid to partially repleted eNOS (still $BH_4$ deficient) causes a substantial reduction in the amount of superoxide adducts (FIG. 4).

NO-Production by eNOS

Figure 5:
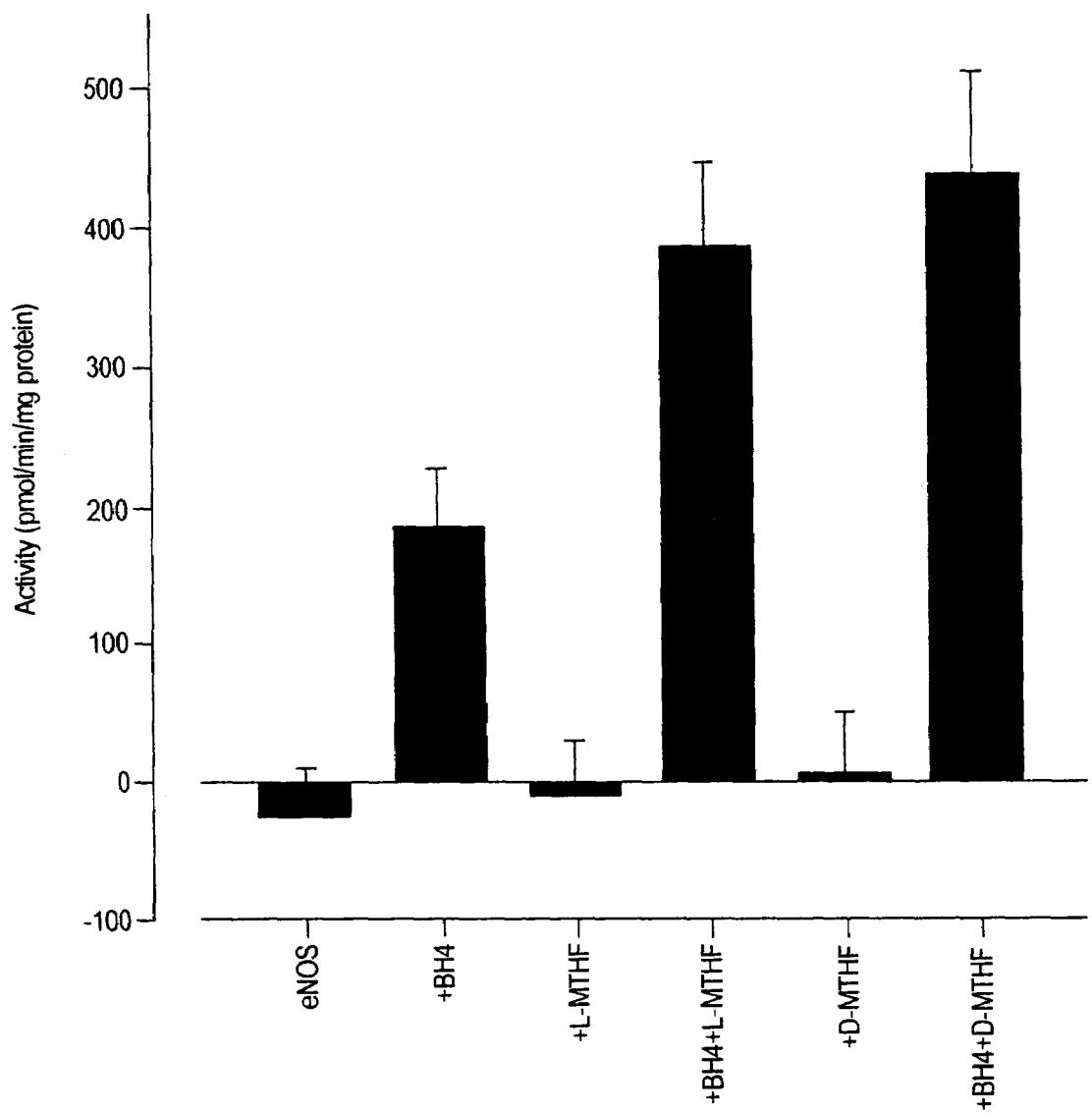
FIG. 5 shows the effect of 5-methyl-(6S)- and -(6R)-tetrahydrofolic acid and tetrahydrobiopterin ($BH_4$) on NO production. Pterin-free eNOS produces no NO. Addition of $BH_4$ results in significant NO production. Both 5-methyl-(6S)- and -(6R)-tetrahydrofolic acid cause a further increase in NO-production by pterin-repleted eNOS, whereas 5-methyltetrahydrofolic acid has no effect on pterin-free eNOS.

The NO production by pterin-free eNOS is located at the detection limit of the arginine-citrulline conversion assay (FIG. 5). Addition of 5-methyl-(6S)- or -(6R)-tetrahydrofolic acid (100 μM final) to pterin-free eNOS has no significant effect on NO production (FIG. 5). In contrast, in pterin-repleted eNOS, two significant differences arise: first, a clear basal NO-production is observed (FIG. 5). Second, the addition of both 5-methyl-(6S)- or -(6R)-tetrahydrofolic acid (100 μM final) causes a significant increase in NO production (FIG. 5; $p<0.05$ vs. $BH_4$ alone).

NO-Production by Endothelial Cells

Figure 6:
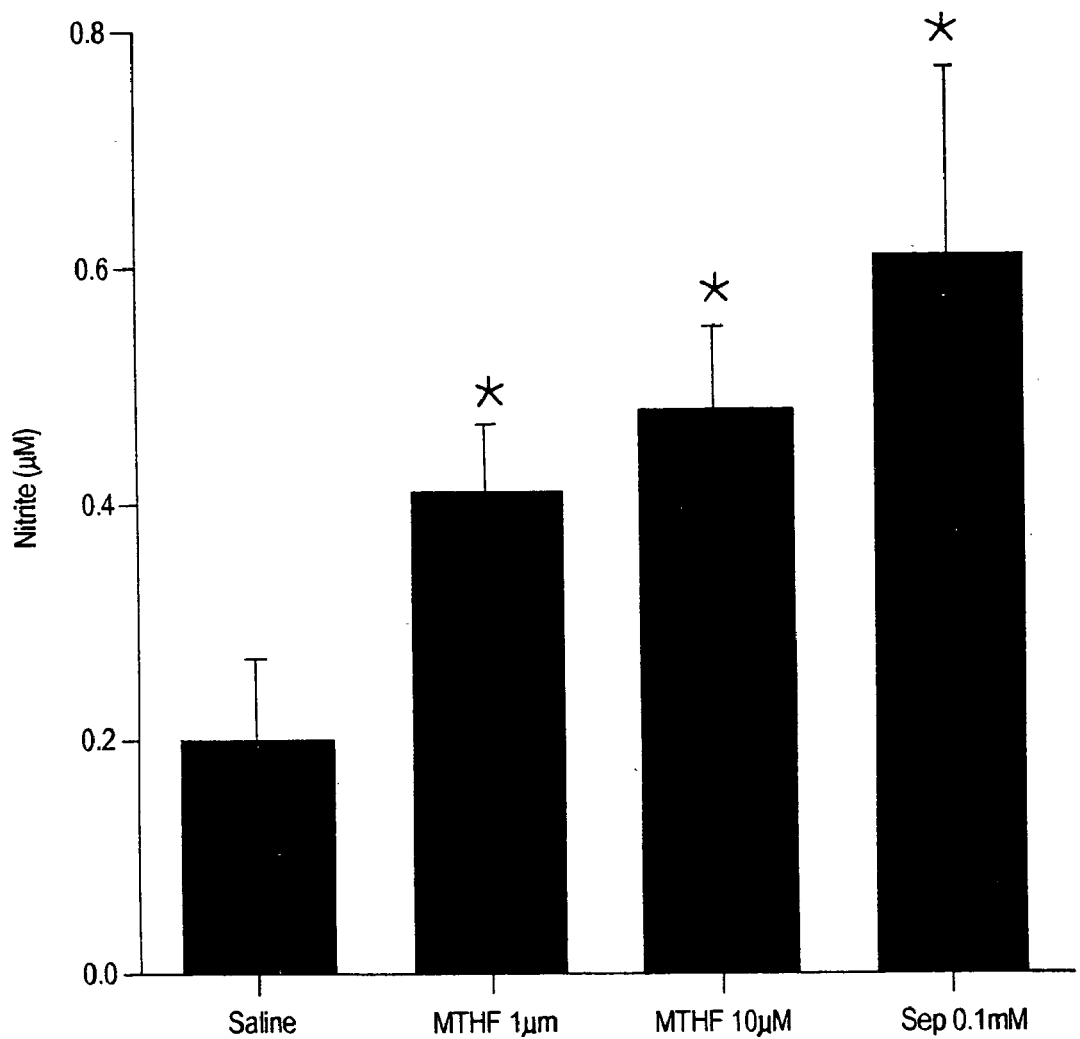
FIG. 6 shows the effect of 5-methyl-(6S)-tetrahydrofolic acid and sepiapterin on acetylcholine-stimulated nitrite production by endothelial cells. Preincubation with 5-methyltetrahydrofolic acid (1 and 10 $\mu M$) o sepiapterin (100 $\mu M$) significantly enhances acetylcholine-induced nitrile production from endothelial cells. *$p<0.05$ vs. saline.

Preincubiation with 5-methyltetrahydrofolic acid did not affect nitrite release in unstimulated endothelial cells. Acetylcholine stimulation caused a significant increase in nitrite release (FIG. 6). Preincubation of endothelial cells with 5-methyl-(6S)-tetrahydrofolic acid and sepiapterin resulted in a significant-further increase in acetylcholine-induced nitrite production (FIG. 6).

The pterin-repleted eNOS used in our studies shows substantial basal production of both NO as well as superoxide and therefore should be considered as $BH_4$ deficient, i.e. partially uncoupled. Under these conditions, addition of folic acid, a folate or a derivative thereof increases NO production. Both diastereoisomeric forms of the folates and derivatives thereof have the same effect. At the same time, the formation of DEPMPO superoxide adducts is strongly reduced by both folic acid, a folate or a derivative thereof.

The reduction of adduct formation caused by folic acid, a folate or a derivative thereof by far exceeds that observed in the HX/XO system. This shows that the major impact of folic acid, a folate or a derivative thereof must be a direct interference with the enzymatic superoxide production by the pterin-repleted eNOS. Again, both diastereoisomeric forms of the folates have comparable effects. Combining the results, for NO and superoxide, the enzymatic activity of pterin-repleted eNOS is highly sensitive to the presence of folic acid, a folate or a derivative thereof. The overall effect is a substantial shift from superoxide production towards NO production. From FIG. 2, we estimate that superoxide production by eNOS is reduced by a factor of 2 at a concentration of [5-methyltetrahydrofolic acid]=50 $\mu$M, i.e. ca. 200 5-methyltetrahydrofolic acid molecules per eNOS dimer. Similar molecular ratios of 5-methyltetrahydrofolic acid vs. eNOS can be achieved in vivo upon oral supplemeatation with folic acid, a folate or a derivative thereof.

5-Methyltetrahydrofolic Acid-Pterin Interaction

It has been shown that folic acid, a folate or a derivative thereof, requires $BH_4$ before it can affect the enzymatic activity of eNOS. Folic acid, a folate or a derivative thereof supports the action as a cofactor of $BH_4$.

Moreover, therapy with folic acid, a folate or a derivative thereof did not show any effect on biopterin levels in vivo. Therefore folic acid, a folate or a derivative thereof exerts its effect via enhanced binding of $BH_4$ to eNOS.

Folic acid, a folate or a derivative thereof act as facilitator of the oxidation of $BH_4$ to the $BH_4$-radical.

5-Methyltetrahydrofolic Acid-endothelial Cells

It has been shown that the effects of folic acid, a folate or a derivative thereof on endogenous, eNOS in endothelial cells are compatible with the findings on the recombinant enzyme. In particular, it has been shown an enhanced T40 status in cultured endothelial cells upon 5-methyltetrahydrofolic acid suppletion.

The decreased superoxide production and enhanced NO synthesis by the nitric oxide synthase (NOS) following the application of folic acid, a folate or a derivative thereof provides a plausible explanation for the increased NO bioavailability in humans upon 5-methyltetrahydrofolic acid suppletion during dyslipidaemia.

Example 1

A tablet containing 50 mg
5-formyl-(6S)-tetrahydrofolic acid and 50 mg
(6R)-tetrahydrobiopterin ($BH_4$)

A mixture of 665 g of the pentahydrate of the calcium salt of 5-formyl-(6S)-tetrahydrofolic acid (corresponding to 500 g 5-formyl-(6S)-tetrahydrofolic acid), 645 g (6R)-tetrahydrobiopterin dihydrochloride (corresponding to 500 g (6R)-tetrahydrobiopterin), 4 kg lactose, 1.2 kg starch, 0.2 kg talc and 0.1 kg magnesium stearate is pressed to form tablets, so that each tablet contains 50 mg 5-formyl-(6S)-tetrahydrofolic acid and 50 mg (6R)-tetrahydrobiopterin ($BH_4$).

The tablet can be coated as a film tablet or can be ground and used in capsule form.

Example 2

A suppository containing 500 mg
5-methyl-(6S)-tetrahydrofolic acid and 500 mg
(6R)-tetrahydrobiopterin ($BH_4$)

A mixture of 632 g of the pentahydrate of the calcium salt of 5-methyl-(6S)-tetrahydrofolic acid (corresponding to 500 g 5-methyl-(6S)-tetrahydrofolic acid), 645 g (6R)-tetrahydrobiopterin dihydrochloride (corresponding to 500 g (6R)-tetrahydrobiopterin), 50 g hydroxy-propylcellulose and 2 kg of semisynthetic glycerides is melted to form suppositories, so that each suppository contains 500 mg 5-methyl-(6S)-tetrahydrofolic acid and 500 mg (6R)-tetrahydrobiopterin ($BH_4$).

Example 3

An injection solution containing 5 mg 5-methyl-
(6S)-tetrahydrofolic acid, 1 mg (6R)-tetrahydro-
biopterin ($BH_4$) and 5 mg L-arginine 5.0 g 5-methyl-(6S)-tetrahydrofolic acid, 1.0 g (6R)-tetrahydrobiopterin ($BH_4$), 5.0 g L-arginine, 10 g glutathione, 30 g citric acid, 160 g mannitol, 1 g methyl-p-hydroxybenzoic acid, 17.7 g sodium hydroxide (or the requisite amount in order to obtain a pH of the solution of 7.3 to 7.8) is dissolved in 3 liters of water for injection and introduced into ampoules, so that each ampoule contains 5 mg 5-methyl-(6S)-tetrahydrofolic acid, 1 mg (6R)-tetrahydrobiopterin ($BH_4$) and 5 mg L-arginine.

Example 4

An Injectable Lyophilisate Containing 1 mg
Tetrahydrofolic Acid and 1 mg Tetrahydrobiopterin
($BH_4$)

A solution of 1.05 g of the sodium salt of tetrahydrofolic acid (corresponding to 1.0 g tetrahydrofolic acid) and 1.40 g (6R)-tetrahydrobiopterin sulfate (corresponding to 1.0 g (6R)-tetrahydrobiopterin) in 1000 ml double-distilled water is introduced via sterile filtration into ampoules and lyophilised, so that each ampoule contains 1 mg tetrahydrofolic acid and 1 mg tetrahydrobiopterin ($BH_4$).

Tetrahydrofolic acid is very sensitive to oxygen, and stringently oxygen-free conditions therefore have to be employed. The use of an antioxidant such as ascorbic acid may be necessary.

Example 5

An injectable lyophilisate containing 20 mg
5,10-methylene-(6R)-tetrahydrofolic acid and 50
mg (6R)-tetrahydrobiopterin ($BH_4$)

A solution of of the .beta.-hydroxypropyl-cyclodextrin inclusion compound of the sodium salt of 5,10-methylene-(6R)-tetrahydrofolic acid containing 10 g 5,10-methylene- (6R)-tetrahydrofolic acid and 50 g (6R)-tetrahydrobiopterin (BH$_4$) in 2000 ml of double-distilled water is introduced via sterile filtration into ampoules, so that each ampoule contains 20 mg 5,10-methylene-(6R)-tetrahydrofolic acid and 50 mg (6R)-tetrahydrobiopterin (BH$_4$).

The same precautionary measures apply to 5,10-methylene-tetrahydrofolic acid as for tetrahydrofolic acid (preceding Example).

Example 6

A tablet containing 4 mg
5-formyl-(6S)-tetrahydrofolic acid and 10 mg
(6R)-tetrahydrobiopterin (BH$_4$)

A mixture of 53.2 g of the pentahydrate of the calcium salt of 5-formyl-(6S)-tetrahydrofolic acid (corresponding to 40 g 5-formyl-(6S)-tetrahydrofolic acid), 100 g (6R)-tetrahydrobiopterin (BH$_4$), 4 kg lactose, 1.2 kg starch, 0.2 kg talc and 0.1 kg magnesium stearate is pressed to form tablets, so that each table contains 4 mg 5-formyl-(6S)-tetrahydrofolic acid and 10 mg (6R)-tetrahydrobiopterin (BH$_4$).

The tablet can be coated as a film tablet or can be ground and used in capsule form.

Example 7

An injectable lyophilisate containing 10 µg
6-methyl-(6S)-tetrahydrofolic acid and 10 µg
(6R)-tetrahydrobiopterin (BH$_4$)

A solution of 10 mg of the sodium salt of 5-methyl-(6S)-tetrahydrofolic acid and 10 mg (6R)-tetrahydrobiopterin (BH$_4$) in 1000 ml of double-distilled water is introduced, via sterile filtration under an inert gas, into ampoules and lyophilised, so that each ampoule contains 10 µg 5-methyl-(6S)-tetrahydrofolic acid and 10 µg (6R)-tetrahydrobiopterin (BH$_4$).

Tetrahydrofolic acid is very sensitive to oxygen, and stringently oxygen-free conditions therefore have to be employed. The use of an antioxidant such as ascorbic acid may be necessary.

Example 8

A tablet containing 15 mg
5-methyl-(6S)-tetrahydrofolic acid and 5 mg
(6R)-tetrahydrobiopterin (BH$_4$)

A mixture of 19.18 g of the pentahydrate of the calcium salt of 5-methyl-(6S)-tetrahydrofolic acid (corresponding to 15 g 5-methyl-(6S)-tetrahydrofolic acid), 5 g (6R)-tetrahydrobiopterin (BH$_4$), 120 g lactose, 21.5 g maize starch, 7.08 g acetylcellulose, 2.28 g diethyl phthalate, 0.64 g silicone HK-15 and 2 g magnesium stearate is pressed to form tablets, so that each tablet contains 15 mg 5-methyl-(6S)-tetrahydrofolic acid and 5 mg (6R)-tetrahydrobiopterin (BH$_4$).

The tablet can be coated as a film tablet or can be ground and used in capsule form.

Example 9

Tablets containing 10 mg
5-methyl-(6S)-tetrahydrofolic acid and 10 mg
(6R)-tetrahydrobiopterin (BH$_4$)

In an analogous manner to that described in Example 8, tablets containing 10 mg 5-methyl-(6S)-tetrahydrofolic acid and 10 mg (6R)-tetrahydrobiopterin (BH$_4$) are produced using maize starch, lactose, magnesium stearate, polyethylene glycol 6000, polymethacrylate, polysorbitol 80, dimethylpolysiloxane, sodium hydroxide and talc.

Example 10

A combination preparation comprising
5-methyltetrahydrofolic acid, tetrahydrobiopterin
(BH$_4$) and arginine A film tablet which contains the following constituents is formulated for preparations for oral application:

| | |
|---|---|
| 25 mg | 5-methyltetrahydrofolic acid |
| 25 mg | tetrahydrobiopterin (BH$_4$) |
| 250 mg | arginine |
| | pharmaceutically compatible adjuvant substances |

The tablet can be coated as a film tablet or can be ground and used in capsule form.

This combination preparation may also be formulated as a solution, e.g. for parenteral application.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising
   (1) folic acid or a folate;
   (2) tetrahydrobiopterin (BH$_4$);
   (3) arginine
wherein arginine is present in a unit dosage of 1 mg to 250 mg.

2. The composition as defined in claim 1 wherein folic acid or a folate is folic acid (pteroylmonoglutamate), one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or salt.

3. The composition as defined in claim 1 wherein folate is the natural diastereoisomer of folate.

4. The composition as defined in claim 1 wherein folate is
dihydrofolic acid,
tetrahydrofolic acid,
5-methyltetrahydrofolic acid,
5,10-methylenetetrahydrofolic acid,
5,10-methenyltetrahydrofolic acid,
5,10-formiminotetrahydrofolic acid,
5-formyltetrahydrofolic acid (leucovorin),
10-formyltetrahydrofolic acid,
10-methyltetrahydrofolic acid,
pharmaceutically compatible salts thereof, or a combination of two or more thereof.

5. A composition according to claim 1, in combination with at least one active substance or at least one adjuvant substance.

6. A composition according to claim 5, wherein the active substance is pharmaceutically compatible active substance.

* * * * *